United States Patent [19]
Twardowski et al.

[11] Patent Number: 5,509,897
[45] Date of Patent: Apr. 23, 1996

[54] MULTIPLE LUMEN CATHETER FOR HEMODIALYSIS

[75] Inventors: Zbylut J. Twardowski; John C. Van Stone; W. Kirt Nichols, all of Columbia, Mo.

[73] Assignee: The Curators of the University of Missouri, Columbia, Mo.

[21] Appl. No.: 389,283

[22] Filed: Feb. 15, 1995

Related U.S. Application Data

[60] Division of Ser. No. 45,016, Apr. 8, 1993, Pat. No. 5,405, 320, which is a continuation-in-part of Ser. No. 772,613, Oct. 8, 1991, Pat. No. 5,211,983, which is a continuation of Ser. No. 461,684, Jan. 8, 1990, abandoned.

[51] Int. Cl.$^6$ ................................................ A61M 3/00
[52] U.S. Cl. ................................................ 604/43; 604/49
[58] Field of Search .......................... 604/43, 264, 275, 604/280, 281, 175

[56] References Cited

U.S. PATENT DOCUMENTS

| | | |
|---|---|---|
| 3,612,038 | 10/1971 | Halligan . |
| 3,890,977 | 6/1975 | Wilson . |
| 3,935,857 | 2/1976 | Co . |
| 4,117,836 | 10/1978 | Erickson . |
| 4,292,976 | 10/1981 | Banka . |
| 4,385,631 | 5/1983 | Uthmann . |
| 4,392,855 | 7/1983 | Oreopoulos et al. . |
| 4,405,313 | 9/1983 | Sisley et al. . |
| 4,531,933 | 7/1985 | Norton et al. . |
| 4,568,329 | 2/1986 | Mahurkar . |
| 4,581,012 | 4/1986 | Brown et al. . |
| 4,681,564 | 7/1987 | Landreneau . |
| 4,681,570 | 7/1987 | Dalton . |
| 4,687,471 | 8/1987 | Twardowski et al. . |
| 4,694,838 | 9/1987 | Wijayarthna et al. . |
| 4,701,159 | 10/1987 | Brown et al. . |
| 4,735,620 | 4/1988 | Ruiz . |
| 4,772,269 | 9/1988 | Twardowski et al. . |
| 4,790,809 | 12/1988 | Kuntz . |
| 4,834,709 | 5/1989 | Banning et al. . |
| 4,846,814 | 7/1989 | Ruiz . |
| 4,867,742 | 9/1989 | Calderon . |
| 4,895,561 | 1/1990 | Mahurkar . |
| 4,935,004 | 6/1990 | Cruz . |
| 4,961,731 | 10/1990 | Bodicky et al. . |
| 4,981,477 | 1/1991 | Schon et al. . |
| 4,985,014 | 1/1991 | Orejola . |
| 5,016,640 | 5/1991 | Ruiz . |
| 5,053,023 | 10/1991 | Martin . |
| 5,156,592 | 10/1992 | Martin et al. . |
| 5,171,216 | 12/1992 | Dasse et al. . |

FOREIGN PATENT DOCUMENTS

| 0132344 | 1/1985 | European Pat. Off. . |
|---|---|---|

Primary Examiner—John D. Yasko
Attorney, Agent, or Firm—Gerstman, Ellis & McMillin, Ltd.

[57] ABSTRACT

A catheter for hemodialysis comprises a flexible catheter tube defining a plurality of separate lumens. The catheter defines an arc angle of generally U-shape in its natural, unstressed configuration. Thus, the catheter may be implanted with a distal catheter portion residing in a vein of the patient, the distal catheter portion being of substantially the shape of the vein in its natural, unstressed condition. Also, a proximal catheter portion resides in a surgically created tunnel extending from the vein and through the skin of the patient, this section of the Catheter also being typically in its natural, unstressed condition. Thus blood may be removed from the vein through one lumen of the catheter, and blood may be returned to the vein through another lumen of the catheter, while the catheter is subject to long term indwelling in the body. Improved results are achieved because of the lack of mechanical stress in the shape of the catheter, which stress causes the catheter to press unduly against adjacent tissues.

7 Claims, 12 Drawing Sheets

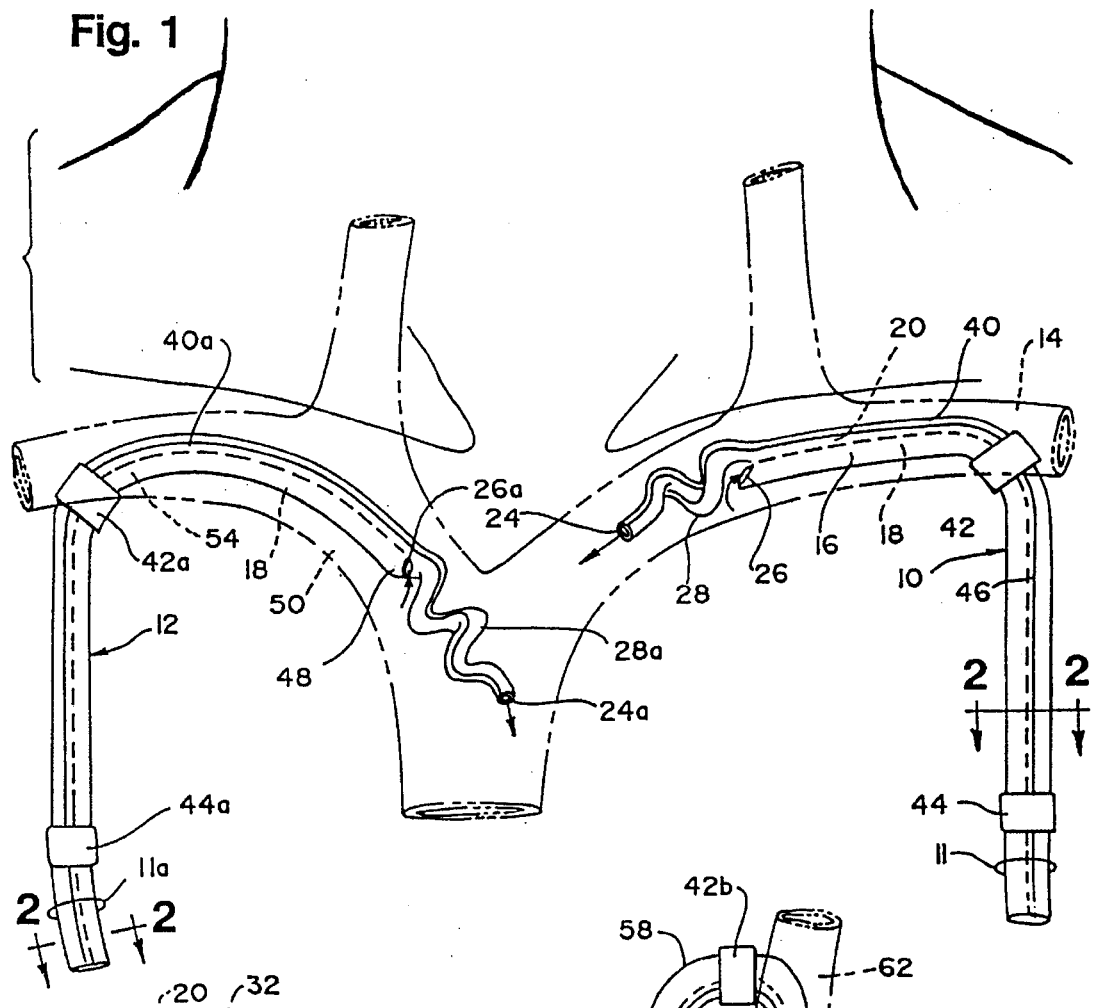
Fig. 1
Fig. 1A
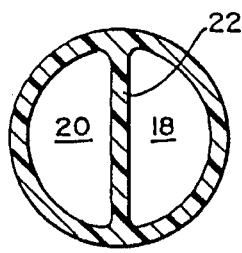
Fig. 2
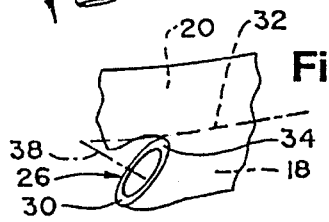
Fig. 3

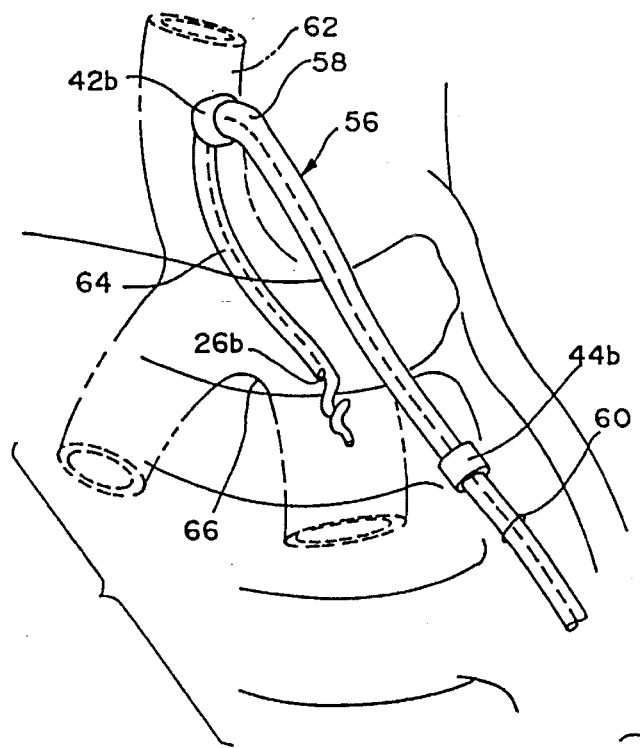
Fig. 4
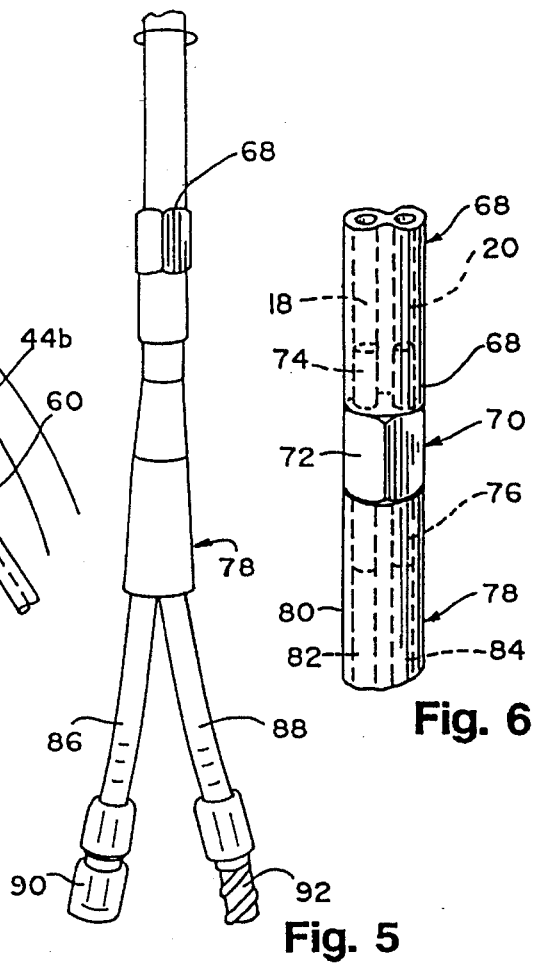
Fig. 5
Fig. 6
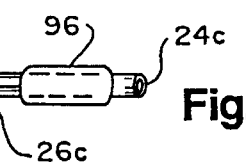
Fig. 7
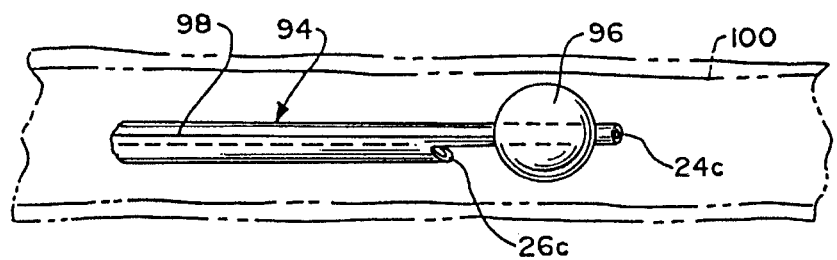
Fig. 8

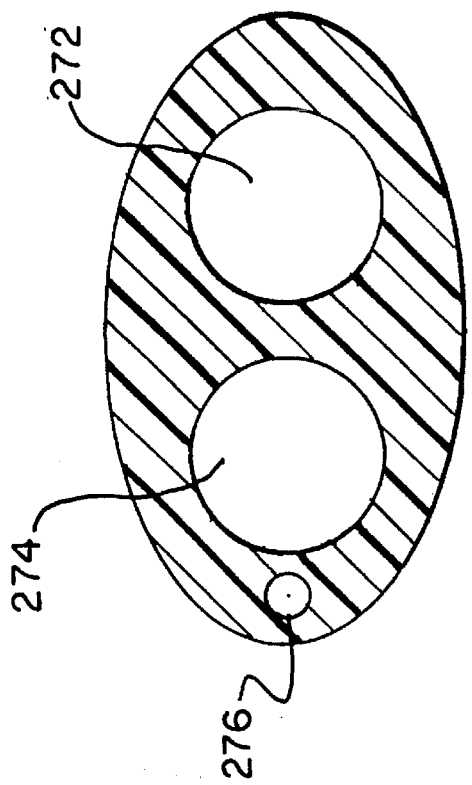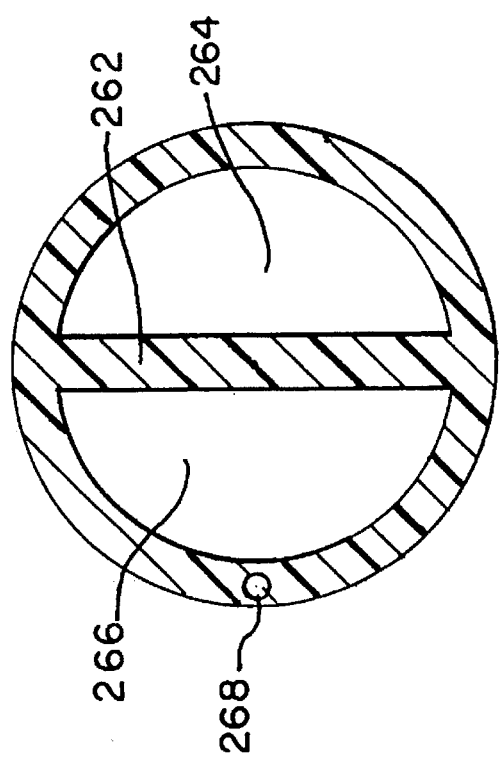

MULTIPLE LUMEN CATHETER FOR HEMODIALYSIS

CROSS REFERENCE TO RELATED APPLICATIONS

This is division of application Ser. No. 08/045,016, filed Apr. 8, 1993, now U.S. Pat. No. 5,405,320, which is a continuation-in-part of application Ser. No. 07/772,613, filed Oct. 8, 1991, now U.S. Pat. No. 5,211,983, which is a continuation of application Ser. No. 07/461,684, filed Jan. 8, 1990, now abandoned.

BACKGROUND OF THE INVENTION

Double lumen catheters have been used as permanent blood access devices for easy and safe access to a patient's arteriovenous system for hemodialysis. Such double lumen catheters have been clinically used and commercially sold. One example of such double lumen catheters is disclosed in Mahurkar U.S. Pat. No. 4,568,329, with other examples of such catheters being disclosed as cited references in that patent.

The use of an indwelling hemodialysis catheter has significant advantages. Particularly, the patient does not have to endure a needle puncture to gain access to his arteriovenous system in every dialysis procedure, but, rather, the indwelling catheter can be simply periodically hooked up to the dialyzer system to provide a blood flow path between the patient and the dialyzer system.

However, as a disadvantage, indwelling catheters which connect to the arteriovenous system are subject to risks of infection and clotting.

Additionally, with a multiple lumen catheter, one lumen serves as a blood outflow path from the arteriovenous (A.V.) system and another lumen serves as an inflow passage for blood to be returned to the A.V. system. As a continuing problem with multiple lumen hemodialysis catheters, the suction at the entrance of the outflow port through which blood flows can cause the outflow port to be occluded by intimal tissues within the vein. This, in turn, can cause tissue damage and results in clotting, which has significantly limited the use of multiple lumen indwelling catheters for hemodialysis.

Furthermore, most multiple-lumen hemodialysis catheters are semi-rigid, with a result that they cannot be anchored securely, and consequently are prone to piston-like movements while they indwell a vein. This movement inside the vein tends to further irritate the intima of the vein wall tissue, leading to further clot formation and vein inflammation. Likewise, outward movements of the subcutaneous and external segments of such a catheter tend to collect contaminants, and to infect the subcutaneous tunnel through the tissue as these segments once again move inwardly.

Other hemodialysis catheters are more flexible, but are molded and cured in a generally straight configuration. Such catheters, however, are usually installed into the venous system in a substantially curved position. Thus, the elastic memory of these catheters causes them to press against some of the vein intima in certain places, with a resulting irritation thereof, and an increase in clotting potential. Likewise, it has been found that catheters which press against the vein walls also uncover vessel wall collage, which attract and activate platelets and the clotting system for an increase in clotting potential, which can cause catheter occlusion by clot attachment to the vein wall, subsequent fibrosis of the clot, and vein stenosis.

By this invention, a multiple-lumen, intravenous catheter, particularly for hemodialysis and also for any other desired use, is provided. The outflow port of the catheter, where a suction is developed, is protected against engagement with the vein intima tissues and the like.

Additionally, the catheter of this invention may be of a desired, curved configuration in its as-manufactured, unstressed configuration, so that the catheter occupies its indwelling site with less irritation of the vein or duct walls, wherever the catheter may be emplaced. The result of this is a catheter which is less likely to generate blood clotting or tissue irritation, and also with a reduction in its potential for causing infection. Such an indwelling catheter may thus be carried by a patient on hemodialysis for long-term use, providing the patient with relief from the anxiety and pain of the normal and frequent needle sticks that are required to accomplish hemodialysis with an A.V. fistula, and facilitating the hemodialysis procedure in other ways as well.

DESCRIPTION OF THE INVENTION

By this invention, a multiple lumen catheter for hemodialysis or the like is provided. The catheter has a distal end portion in which at least a pair of the catheter lumens each communicate with the exterior through aperture means.

In accordance with this invention, the aperture means of one of the lumens defines a first port at essentially the distal catheter end. The aperture means of the other of the lumens defines a second port spaced proximally along the catheter from the distal end and first port. In one embodiment, the second port is defined by a substantially angular wall which has a radially outer portion relative to the catheter axis that is positioned slightly closer to the catheter distal end than a radially inner portion of the same substantially angular wall. The, result of this is that the second port faces radially inwardly to a degree, with the axis of the second port being angled radially inwardly at an acute arc angle to the catheter axis.

By this means, the second port, which is preferably used as the suction port for withdrawing blood through the catheter for the hemodialyzer or other medical device, operates with a significant reduction of possibility that intimal tissue along the blood vessel walls may be captured by suction at the second port. This protects the delicate intimal tissues, and reduces the possibility of clotting, irritation, and infection, while still providing an adequately-sized aperture to draw blood into the catheter for processing by medical apparatus.

The blood is then typically returned through the lumen that connects with the first port, the first port being longitudinally spaced from the second port so that returning blood can be distributed away from the second, suction port, to minimize immediate recycling of the processed blood.

Further in accordance with this invention, the one lumen which connects with the first port comprises a portion that extends distally beyond the second port. This one lumen portion which extends distally beyond the second port is preferably defined by a distal catheter portion which is of substantially helical shape. Such a helical catheter portion can serve to generally keep the distal end of the catheter away from the sides of the vein walls (or other blood vessel or duct walls as the case may be), particularly when the diameter of the helical section exceeds the catheter diameter. As the result of this, particularly the second port and also the first port may be held in spaced relation from the blood vessel walls. Thus this helical catheter portion is an alternative or additional means for preventing suction of the blood vessel intima into the second port.

Also, the catheters of this invention preferably have a section thereof which defines an arc angle of at least about 90 degrees, and, if desired, up to about 180 degrees. This angled section is preferably spaced from and proximal to the second port. As additional embodiment, a length of such a catheter which is positioned between the angled section and the second port defines an arc in the dimension perpendicular to the plane defined by the arc angle in the section. Both the angled section and the arc may be proportioned so that the flexible catheter, in its unstressed, as-manufactured configuration, can provide improved registry with the shape of the blood vessel in which the length of the catheter resides. Thus, such a catheter will exhibit less pressure and abrasion against the blood vessel walls, providing conditions under which less clotting and tissue irritation will take place. This, in turn, provides a catheter which is capable of long-term indwelling in the A.V. system of a patient.

As another modification, the catheter of this invention may define an inflatable balloon positioned between the first and second ports. The balloon may be inflatable to a size which is large enough to limit engagement of the second port with a wall of the blood vessel (or duct) in which the catheter resides, but which is small enough to avoid complete occlusion of the blood vessel or duct. Additionally, a conventional inflation lumen may be provided in the catheter, with the inflation lumen communicating with the balloon to permit inflation and deflation thereof from a fluid source at the proximal end of the catheter. By this means, the balloon can serve to approximately center the first and second ports from vessel or duct walls, which is particularly desirable with respect to the second port for the reasons described above.

Further in accordance with this invention, catheters of the types described above, as well as other catheters, may be of specific, desired shapes as described below in their unstressed, as-manufactured configurations for obtaining the desired improved registry with the shape of the blood vessel in which the length of the catheter resides. Thus, such catheters exhibit less pressure and abrasion against the blood vessel walls for the advantages of reduction in clotting and tissue irritation as described above.

Specifically, such catheters are preferably proportioned to be implanted in a major vein of the patient, with the distal tip of the catheter being positioned in the right atrium of the heart. This provides a high and turbulent blood flow to the catheter distal tip, as well as a bigger chamber, which minimizes the chances for the catheter distal tip to press against the wall thereof.

In this invention, catheters are provided, preferably being used for long-term access for hemodialysis. These catheters may be implanted so that their distal tip is inserted into the right atrium of the heart through one of the following veins, for example: The right internal jugular vein, the left internal jugular vein, the right subclavian vein, or the left subclavian vein.

Catheters of this invention may also be inserted into the common iliac veins through femoral veins, these catheters being typically provided for intermediate term blood access.

The tributaries of the superior vena cava are preferred for long term catheter implantation because of the relatively short distance to the right atrium of the heart, the minimal range of shape changes of these veins with natural movements of the patient (to minimize the damage to the vessel intima), and because of good acceptance by the patients of the skin exit on the thoracic wall.

Typically, the femoral veins are less suitable for prolonged use because of a substantial range of shape change of the veins with walking and the like. However, for patients who are confined in bed or who need blood access for only a limited time, this route will save more permanent sites such as the jugular and subclavian for later use. Also, the femoral veins are easy to cannulate, so that catheters of this invention may be inserted into the femoral veins at the bed side.

The catheters of this invention comprise a flexible catheter body which may be made of silicone rubber, medical grade polyurethane, or the like. The catheter body defines a pair of lumens, one for inflow and the other for outflow of blood to and from the patient. The distal end portion of the catheter is implanted deep in the patient, preferably in the right atrium as stated, while the proximal end portion of the catheter is adapted for connection and blood flow communication with a hemodialyzer or hemofilter, for example. Typically, the catheter is also provided with typically one or two ingrowth cuffs, which are bands of fabric carried by the catheter body to permit fibrous tissue ingrowth in the surgically-created catheter tunnel.

After implantation in the patient, the catheter comprises three segments. Specifically, the intravenous catheter segment is the part of the catheter located within a vein. The intramural catheter segment is the part of the catheter located within the surgically-created tunnel between the vein and the skin. The external catheter segment is the part of the catheter outside of the skin exit.

Preferably, the lumen for outflow of blood at the distal catheter end terminates approximately 0.5–3 cm beyond the end of the lumen for inflow of blood, to prevent significant blood recirculation in the dialyzer.

To decrease or eliminate the chances of the distal inflow lumen end from attaching to the vein wall by suction, the outflow tubing extending beyond the inflow lumen distal end may be provided with features to prevent this occurrence with any of the following features: (1) The inflow bore opening is directed toward the outflow tubing and away from the vessel wall; (2) Using a helical pigtail shaped section; or (3) the presence of a balloon, which may be collapsed in periods between dialysis and inflated only during dialysis through an additional, small lumen in the catheter.

The dimensions of the catheters used here are preferably chosen to match the vein in which each catheter is to be implanted. The dimensions and shapes of the veins are dependent upon the body size: e.g., height, weight, and distance from the sternal notch to the xiphoid process (a measure of chest length), and the intrachromal distance (a measure of the upper body width). Catheters of identical design but different size in accordance with this invention may be made in preferably at least three sizes for each vein. Thus, a wide range of patient sizes can be accommodated.

While the distal aperture means of the respective flow lumens of this catheter may utilize a plurality of side ports as a supplement to, or substitute for, the end-mounted first and second ports, such is generally deemed undesirable for the following reason:

Between usages, the indwelling catheter of this invention exhibits stagnant flow conditions within its respective lumens. Such flow conditions are of course conducive to blood clotting, so, typically, such a catheter is filled with heparin solution between usages. The presence of side ports will tend to increase the diffusion and replacement of the heparin with blood between catheter usages, which can increase the possibility that clotting can take place in the blood which finds its way into the catheter lumens and then sits in a stagnant manner. The use of single, first and second ports in the manner described herein can reduce this possibility.

DESCRIPTION OF DRAWINGS

In the drawings, FIG. 1 is a diagrammatic view of a pair of multiple-lumen, I.V. catheters of this invention, each shown to be installed in, respectively, the right or left brachycephalic vein through the respective subclavian veins, a distal portion of each catheter only being shown;

FIG. 2 is an enlarged, sectional view taken along each of lines 2—2 of FIGS. 1;

FIG. 3 is an elevational view of an indwelling catheter in accordance with this invention, implanted into a brachycephalic vein through the right internal jugular vein, with only a distal portion of the catheter being shown;

FIG. 4 is an elevational view similar to FIG. 3, but rotated approximately 90 degrees about the vertical axis;

FIG. 5 is an elevational view of the proximal portion of the catheters illustrated in FIGS. 1–4;

FIG. 6 is an enlarged, elevational view, showing internal structure, of the junction between the intravenous catheter of this invention and the pair of tubular extensions thereof carried at the proximal catheter end;

FIG. 7 is an elevational view of the distal end of another embodiment of the catheter of this invention;

FIG. 8 is an elevational view similar to FIG. 7, but showing the catheter emplaced in a blood vessel and with the balloon fully inflated;

FIGS. 18 and 19 are each transverse sectional views of differing embodiments of the catheter of this invention.

DESCRIPTION OF SPECIFIC EMBODIMENTS

Figure 9:
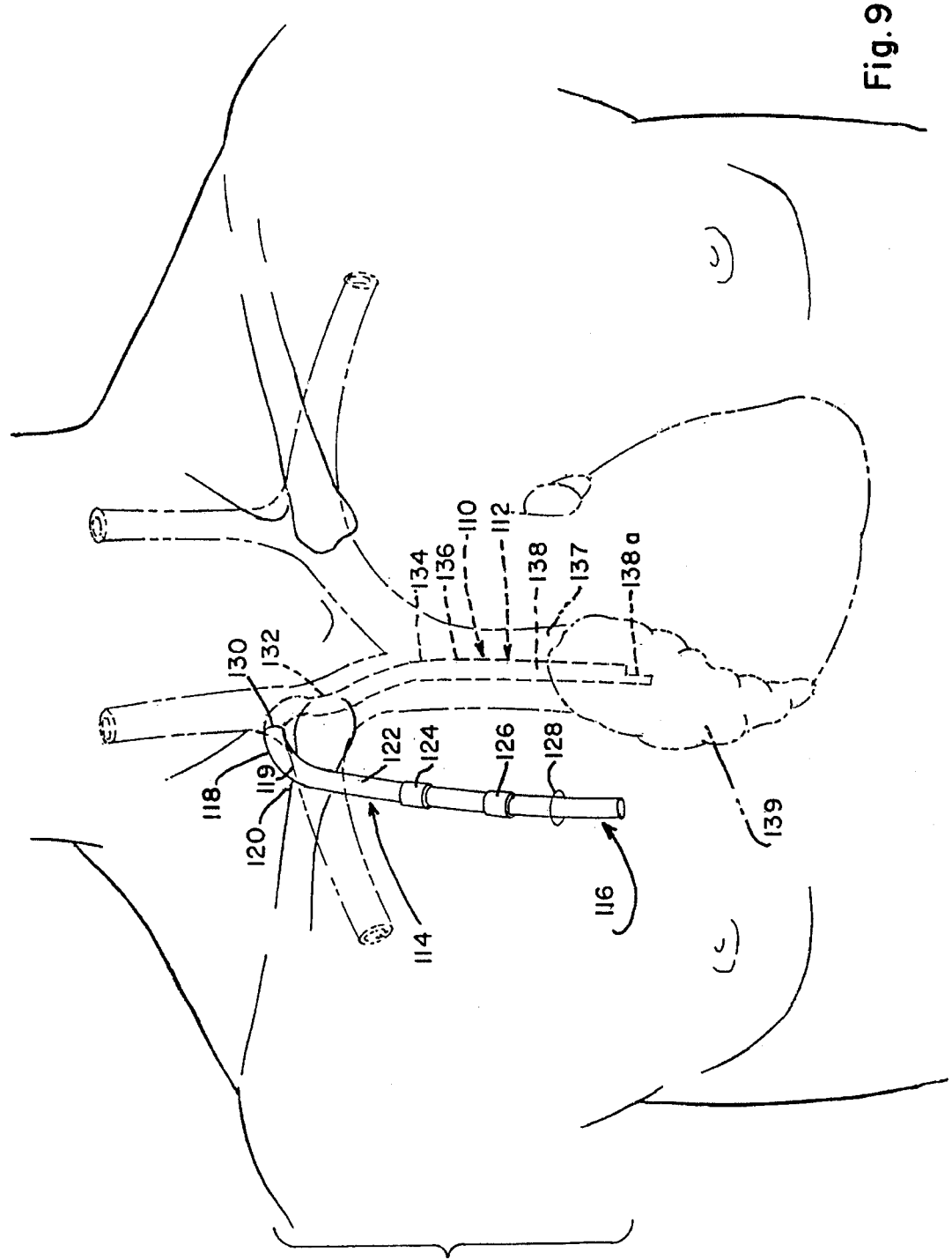
FIG. 9 is an elevational view of another embodiment of the catheter of this invention shown implanted in the right atrium through the right jugular vein.

Referring to the drawings, FIG. 1 shows the outline of an human upper torso, shoulders, and neck, and some of the major veins of the area, in phantom, with two multiple lumen I.V. catheters of this invention shown to be emplaced in indwelling manner. This arrangement is primarily for purposes of illustration since, under normal circumstances, no more than one indwelling catheter will be implanted in a patient at one time.

Double-lumen indwelling catheters 10, 12 may be made of a flexible plastic material such as silicone or polyurethane elastomers, defining a double lumen in the manner of FIG. 2.

Catheter 10 extends through a surgically formed tissue tunnel from an entry port 1 at the skin, through to an aperture cut in vein 14, at which point catheter 10 defines an arc angle of approximately 90 degrees and a vein indwelling portion 16.

Catheter 10 defines a pair of lumens 18, 20, which are separated by a partition 22. Lumen 20 extends to the distal end of catheter 10 and terminates in a first open port 24, while lumen 18 terminates in a second port 26, port 26 being spaced proximally along catheter 10 from the distal end and first port 24. Additionally, as shown, the portion 28 that extends distally beyond second port 26 is of substantially helical shape, the helical shape being of a diameter slightly larger than the catheter diameter to help prevent second port 26 from engaging the walls of vein 14 and sucking intima as previously described. At the same time, an open flow path is readily available for blood to pass through second port 26 and along lumen 18 through the catheter into a hemodialyzer or the like.

After the hemodialysis of the particular blood portion has been completed, it is returned through lumen 20 of catheter 10, to be expelled out of the distal end thereof through first port 24, so that the expelled blood is longitudinally separated from blood intake port 26, to reduce shunting of processed blood back into the intake port.

Further in accordance with this invention, as particularly shown in the detailed FIG. 1A, second port 26 is defined by a substantially angular wall having a radially outer portion 30, relative to the catheter central axis 32, that is positioned slightly closer to the distal end 24 of catheter 10 than a radially inner portion 34 of the substantially angular wall. Thus the axis 38 of second port 26 is angled radially inwardly at an acute angle to catheter axis 32. As previously stated, the effect of this is to cause second port 26 to be less likely to suck in vein wall intima along with inflowing blood, to avoid tissue damage and consequent clotting or vein irritation.

Catheter 10 is shown in its as-formed, unstressed configuration, although being flexible, it can be straightened out for insertion and packaging. However, because catheter 10 defines an angled section, it can fit into vein 14 without any significant plastic memory attempting to force the catheter into a straight configuration or the like, so that the distal portion 16 of the catheter resides in the vein with less pressure against the vein walls.

Catheter 10 also carries a radiopaque stripe 40 to facilitate location of the catheter by a fluoroscope. Similarly, catheter 10 carries a pair of spaced fabric cuffs 42, 44, being spaced approximately four centimeters apart and adapted to be a site for tissue ingrowth, for long-term securance of catheter 10 in its indwelling position as shown. Both cuffs reside in the tunnel formed through the tissue by the surgeon, with the outer cuff 44 being positioned approximately one centimeter from tunnel exit 11. Catheter portion 46 which resides in the surgical tunnel is preferably directed downwardly, so that tunnel exit contamination such as sweat, dirt, and water tends to stay out of tunnel exit 11, and internal drainage also is facilitated through the tunnel exit. Also, although upper portions of the catheter are near the neck of the patient, the tunnel exit 11 is substantially below the neck in such a configuration.

Accordingly, such an implanted indwelling catheter can remain with the patient for a long period of time, freeing him from the agony of frequent punctures by large needles as normally required in dialysis procedures, while minimizing clotting and tissue irritation.

Turning to catheter 12 of FIG. 1, this double-lumen catheter also defines lumens 18, 20, separated by wall 22. Alternatively, a concentric arrangement of double or multiple lumens may be provided to catheters of this invention, if desired.

As in the embodiment of catheter 10, lumen 20 of catheter 12 terminates at the catheter distal end in a first port 24a, while lumen 18 of catheter 12 terminates in second port 26a. As before, the catheter portion 28a between ports 24a and 26a is of helical shape, to prevent particularly second port 26a from engaging vein intima, to damage them by the suction pressure typically found in port 26a and its lumen 18. In this particular circumstance, the configuration of port 26a is different from port 26, in that port 26a is not inwardly angled as in the previous case of port 26. Rather, it is forwardly angled through a surface of the catheter wall which defines the base 48 of helical portion 28a. Thus, in this circumstance also, second port 26a faces away, to at least an extent, from the walls of vein 50, being also shielded from engagement with vein wall intima by the presence of helical portion 28a, which preferably has a diameter greater than the diameter of the remainder of catheter 12.

As in the previous embodiment, the flexible, resilient catheter 12 is shown in its as-manufactured, unstressed configuration, although it can be straightened our for packaging and insertion. Thus, as before, the catheter in its implanted position can exhibit little or no elastic memory that causes its distal end to press against the vein walls with resulting tissue irritation or damage and consequent generation of blood clots.

The remaining features of catheter 12 are similar to those of the previous catheter 10. Radiopaque stripe 40a and tissue adhesion cuffs 42a, 44a are provided for the same functions as in the previous embodiment. The proximal portion 52 of catheter 12 extends out of tunnel entry site 11a, the tunnel which extends from tunnel exit 11a through the wall of vein 50 being formed by the surgeon.

In the arced area generally indicated by reference numeral 54, catheter 12 defines an arc angle of somewhat greater than 90 degrees. This arc angle is predetermined, plus the curvature of the arc of the catheter between cuff 42a and second port 26a, to accommodate to the shape of vein 50 with minimal vein wall contact.

Turning to FIG. 3, double lumen catheter 56 may be of a design that is substantially identical to that of catheter 10 except for the extent of the arc angle defined by angled section 58. This catheter is also shown in its as-manufactured, unstressed configuration, and defines almost a 180 degree arc angle throughout section 58 so that the catheter may be inserted through a surgical tunnel beginning at exit site 60, and then angled to proceed upwardly through the surgical tunnel to jugular vein 62, and then to permit the distal end 64 thereof to be angled downwardly again. The design of first and second ports 24b, 26b, and helical section 28b may be identical to the design of the corresponding components in catheter 10. Also, catheter 56 may carry a radiopaque stripe 40b and tissue securance cuffs 42b, 44b, for the purposes and advantages previously described.

Thus, in this embodiment also, the suction of blood through second port 26b and its connected lumen is performed with less risk of vein wall damage and consequent clotting and irritation, so that the catheter may function as a long-term indwelling catheter, to achieve the benefits for the dialysis patient as previously described.

FIG. 4 is another view of catheter 56, indwelling the jugular vein 62, taken 90 degrees from the viewpoint of FIG. 3. There, it can be seen that in section 64 of the catheter, the vein indwelling portion positioned between angled section 58 and second port 26b defines an arc in the dimension which is perpendicular to the plane defined by the arc angle in section 58. This is to provide improved compliance with the shape of the blood vessel including jugular vein 62 in which that length of catheter resides, particularly to avoid catheter pressure on a wall section of the venous system, such as wall portion 66.

Turning to FIGS. 5 and 6, the proximal end 68 of any of catheters 10, 12, 56, is shown, the proximal ends 68 of each catheter being identical to each other.

As shown in FIG. 6, the specific proximal catheter end 68 shown is a simple end of the catheter body which defines lumens 18, 20. A double ended, tubular prong member 70 is provided, being made of plastic or the like, having a central, enlarged handle portion 72 and a pair of connector tubes 74, 76, extending through handle portion 72 and projecting out both ends. The respective ends of tubular members 74, 76, are sized to respectively project at one end into lumens 18, 20, in tight, sealing relation. If desired, well known sealing ribs may be provided to the respective ends of tubes 74, 76.

Then, a connector extension member 78 may be provided. The particular connector extension member 78 shown includes a unitary connector base 80 defining a tube with a pair of lumens 82, 84, that are sized to engage their respective ends of connector tubes 74, 76, in a similar tight sealing manner as the opposed ends of connector tubes 74, 76.

Connector base 80 bifurcates into a pair of tubular connector extensions 86, 88, each of which defines a lumen 82, 84 and is terminated with a conventional female luer connector 90, 92, to permit aseptic connection with a dialysis machine or the like, and also to permit connection with a sterile seal cap between uses. Connector 90 is shown to be closed off with a cap, while connector 92 has its cap removed. Typically, extensions 86, 88 are about 7 cm long.

Thus, as previously described, when connectors 90, 92, exhibit wear and need replacement before the indwelling catheter must be replaced, one can simply cut away connector member 78 by severing the proximal end of catheter 68 as proximally far out as possible. Then, a new connector link 70 and connector member 78 may be applied, to provide further useful life for the catheter system.

Referring to FIGS. 7 and 8, an alternative design of catheter 94 is disclosed. Only the distal tip is shown because the remainder of the catheter may be of a conventional design or in accordance with any of the previous embodiments disclosed herein.

Catheter 94 defines a pair of lumens 24c, 26c, which communicate with respective flow ports 24c, 26c, in a manner similar to the previous embodiments. It will be particularly noted that second port 26c is identical in configuration to second port 26 of FIGS. 1 and 1a, and exhibits described advantages of that particular design of second port.

An inflatable balloon 96 is carried on catheter 94, being connected to an inflation lumen 98 that may be of a diameter substantially less than that of the lumens that connect to ports 24c and 26c. Thus, as shown in FIG. 8, balloon 96 may be inflated after placement in a blood vessel 100. Balloon 96 is inflatable to a size which is large enough to limit engagement of second port 26c with the wall of blood vessel 100, but small enough to avoid complete occlusion of the blood vessel, as shown. Balloon 96 is shown diagrammatically, and may also be a conventional sleeve, sealed at both ends to the catheter, being made of a flexible but non-resilient material such as poly(ethylene terephthalate) or nylon.

Accordingly, substantial blood flow can still continue through vein 100, but second port 26c, serving as the blood inlet, is protected from engaging the blood vessel intima along its wall and causing damage through the suction pressure.

It should also be noted that the embodiment of FIGS. 7 and 8 may function in an effective manner without the presence of balloon 96 and lumen 98, relying merely upon the inwardly angled shape of second port 26c to avoid damaging engagement with the intima on the wall of blood vessel 100. Such an embodiment represents a simplified, inexpensive, and preferred embodiment of this invention, since it avoids the expense of fabricating and applying balloon 96 in the manufacture of the catheter, and it also avoids the expense involved in fabricating the helical distal catheter end 28 of the previous embodiments.

As shown in the drawings, the intravenous and intramural segments of the catheters, typically beginning at the deep cuff, are molded with a shape resembling the shape of the vessel which they occupy and the surgical tunnel. As a result of this design, the catheter can be mounted in an arcuate tunnel in relatively unstressed condition, with the bent portion being typically mounted partially in the vein lumen and partially in the tunnel. The cuffs anchor the catheter, minimizing its movements and preventing pericatheter migration of bacteria into the vein lumen.

The outflow lumen tubing may be provided with a radioactive stripe as discussed above. Besides the usual role of facilitating visualization of the catheter on an x-ray, the stripe is also useful during insertion and post implantation care, facilitating recognition of the proper catheter position. Alternatively, the whole body of the catheter may be made radiopaque to facilitate its location on an x-ray.

The skin exit is preferably directed downwardly to decrease chances of sinus tract contamination with down flowing sweat and bacteria-laden water. Also, a downwardly directed exit facilitates pus drainage in the case of infection.

Because of the presence of Y-connector 78, which may be attached to a catheter body during the insertion procedure rather than being an integral part of the catheter, a new method of insertion may be utilized. Currently used catheters require that the cuff be retrograded into the surgically created tunnel through the skin exit. For this purpose the incision in the skin, while as small as possible, has to be large enough to allow the cuff entry. This predisposes to cuff extrusion in the early period post insertion. Moreover, the retrograde insertion of the cuff through a relatively tight skin incision predisposes to cuff contamination with skin bacterial flora, which cannot be completely eliminated even in the best sterilized operative field. Thus, the cuff sometimes becomes overtly infected after a prolonged period of dormant contamination.

With the connector of this invention, the tunnel may be made from the inside of the patient, and the catheter exit may be for the size of the catheter body rather than the larger cuff. Likewise, the cuff does not need to be retrograded through the skin exit. After placement of the catheter, the Y-connector may be attached as described with respect to FIGS. 5 and 6.

Catheters may be inserted under local anesthesia. Catheters for subclavian veins maybe inserted with a peel-away method. A 2–3 cm transverse or longitudinal incision may be made beneath the clavicle and 2–3 cm outside the midclavicular line, through the skin and subcutaneous tissue. The subclavian vein is punctured, and the catheter is inserted with the peel-away technique through the subclavian vein into the brachiocephalic vein, the superior vena cava, and into the right atrium. The catheter position is confirmed by an x-ray. A subcutaneous tunnel is made with a hemostat to the level where the outer cuff will lodge. A small (0.5 cm) punch wound is made for the skin exit, one cm below the superficial cuff position. A special trocar is attached to the catheter, and directed through the exit site. The Y-connector is then attached to the catheter. The catheter patence is verified by simple blood withdrawal and reinfusion, following which the catheter lumens are filled with heparin, urokinase, sodium citrate, sodium chloride, or other solution. The incision is closed with subcuticular sutures. No sutures are preferably placed at the exit.

For insertion of the jugular catheters, a 2–3 cm transverse incision is made above the clavicle through the skin and subcutaneous tissue to expose the vein in the space between the sternal and clavicular heads of the sternocleidomastoid muscle. A purse string suture is placed on the jugular vein, and a small venotomy is made. The catheter is inserted into the vein and advanced through the brachiocephalic vein, the superior vena cava and into the right atrium. The catheter position is confirmed by an x-ray. Alternatively, the catheter may be inserted with the peel away sheath technique. The remainder of the implantation procedure is similar to that for subclavian vein catheters.

The femoral catheter is inserted under local anesthesia. A 2–3 cm transverse or longitudinal incision is made through the skin and subcutaneous tissue beneath the level of the inguinal ligament. The vein is punctured, and the catheter is inserted with a peel-away sheath technique through the femoral vein into the external iliac vein, common iliac vein, and then into the inferior vena cava. The catheter position is confirmed by an x-ray. A short, subcutaneous tunnel is made with a hemostat down to the level where the cuff will lodge. A small (0.5 cm) punch wound is made for the skin exit 1 cm below the cuff position. The trocar is attached to the catheter and directed through the exit site. The Y-connector is then attached to the catheter. The remaining part of the insertion procedure is identical to that of the previous catheters.

Figure 10:
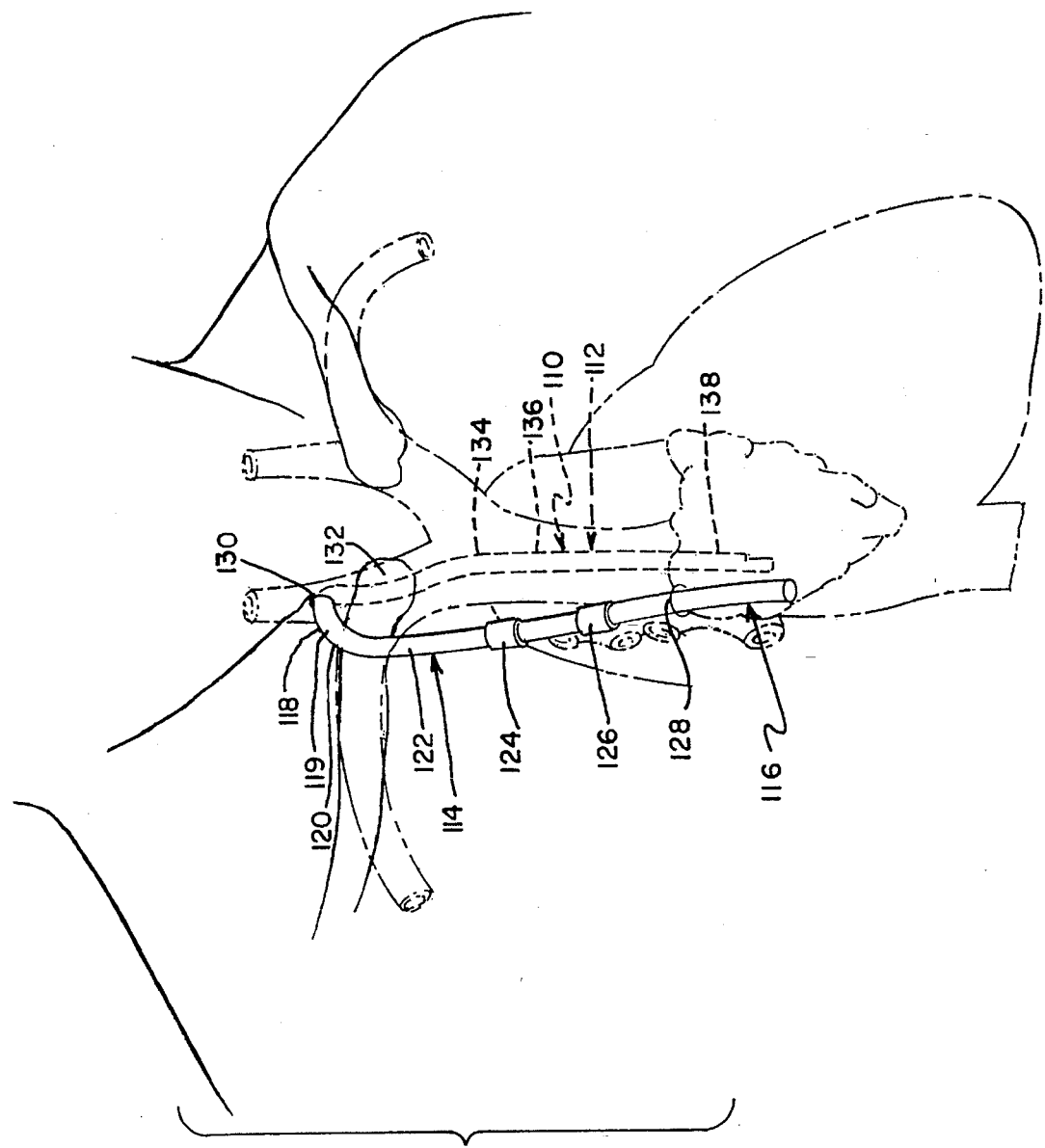
FIG. 10 is an elevational view similar to FIG. 9, but taken on an oblique arc angle therefrom.

Referring now to FIGS. 9 and 10, a catheter for the right jugular vein is depicted in its natural, unstressed configuration as it may preferably be implanted, with its distal end 138 being positioned in the right atrium 139 of the heart. Catheter 110 comprises an intravenous segment 112 which is located in the vein; an intramural segment 114 which is located in a surgically created tunnel between the entrance 130 of the jugular vein and the skin exit 128. Finally, the catheter 110 defines an external portion 116 located outside of skin exit 128.

In the border area of the intravenous and intramural segments, catheter 10 defines, in its natural, unstressed condition, a curved or bent section 118, which is convex cranially (upward) and which typically defines an arc angle of 160°–180°. Proceeding proximally from intravenous segment 112, intramural segment 114 gradually rotates for a bend 119 which can be seen particularly in FIG. 10 to be both in the dimension of the bend of section 118 and also in the dimension perpendicular thereto. This second bent section 119 defines an arc angle of approximately 50–90 degrees while also extending laterally and anteriorly about 5–30 mm until it crosses the right clavicle 120. Then, catheter 10 extends proximally in section 122 down about 20–80 mm and anteriorly at an arc angle of 5°–50° in the sagittal plane and 0°–20° in the coronal plane. This segment 122 is provided with a pair of cuffs 124, 126. Outer cuff 126 is positioned to be located in the surgical tunnel about 5–20 mm from the skin exit 128.

The intravenous segment 112 of catheter 110 extends, from its entrance 130 in the internal jugular vein down approximately 5–30 mm, bending medially about 0°–40° and about 10° posteriorly or anteriorly in the sagittal plane, to enter into the right brachiocephalic vein 132, through which it extends about 5–60 mm to the point of merger of both brachiocephalic veins. At that point, catheter 110 bends laterally in area 134 about 0° to 40° and about 0°–10° posteriorly or anteriorly in the sagittal plane to enter into the superior vena cava 137. From there, catheter 110 extends downwardly another 20–120 mm at an arc angle of 0°–10° posteriorly or anteriorly in the sagittal plane and 0°–10° medially or laterally in the coronal plane, to cause the distal tip 138a of the catheter to reside into the right atrium 139. Thus it is understood that the catheter segment 136 may be straight if desired, but may carry slight bends, as indicated.

Thus, a catheter of the unstressed shape as described, and having the dimensions as indicated, may be successfully implanted in the right jugular vein of patients, to achieve the desirable results of long term catheter implantation without clotting or other ill effects. Also, the distal end 138 of catheter 110 may be of the design as indicated in FIGS. 1 and 1a, except that in this embodiment the helical shape of the forward most portion is replaced with a straight section. It can be seen that this catheter is, in its natural, unstressed condition, of substantially U-shape, but with a curve at area 119 in the third dimension, out of the plane normally occupied by a U-shape.

Figure 11:
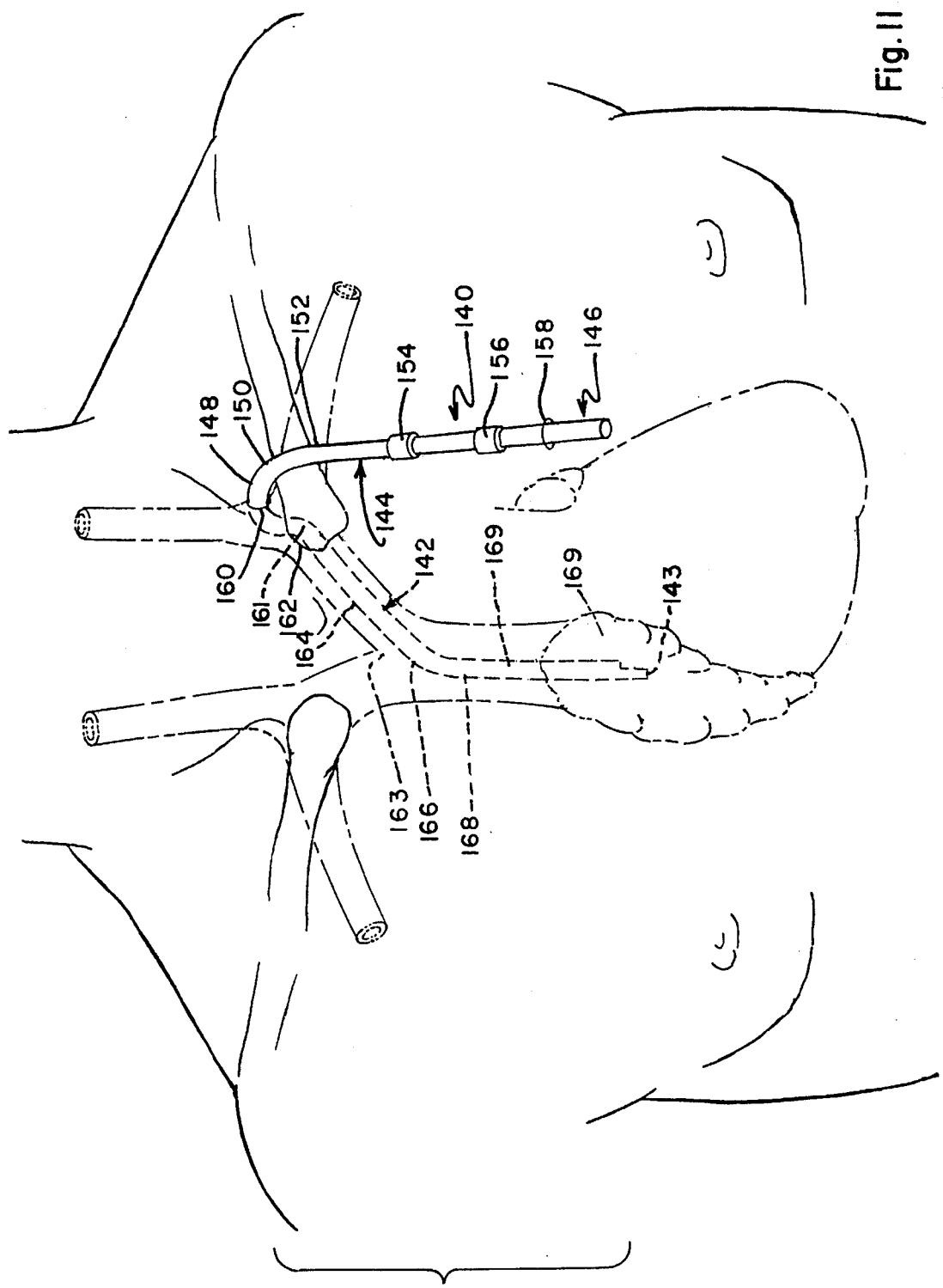
FIG. 11 is an elevational view of another embodiment of the catheter of this invention shown implanted in the right atrium through the left jugular vein.
Figure 12:
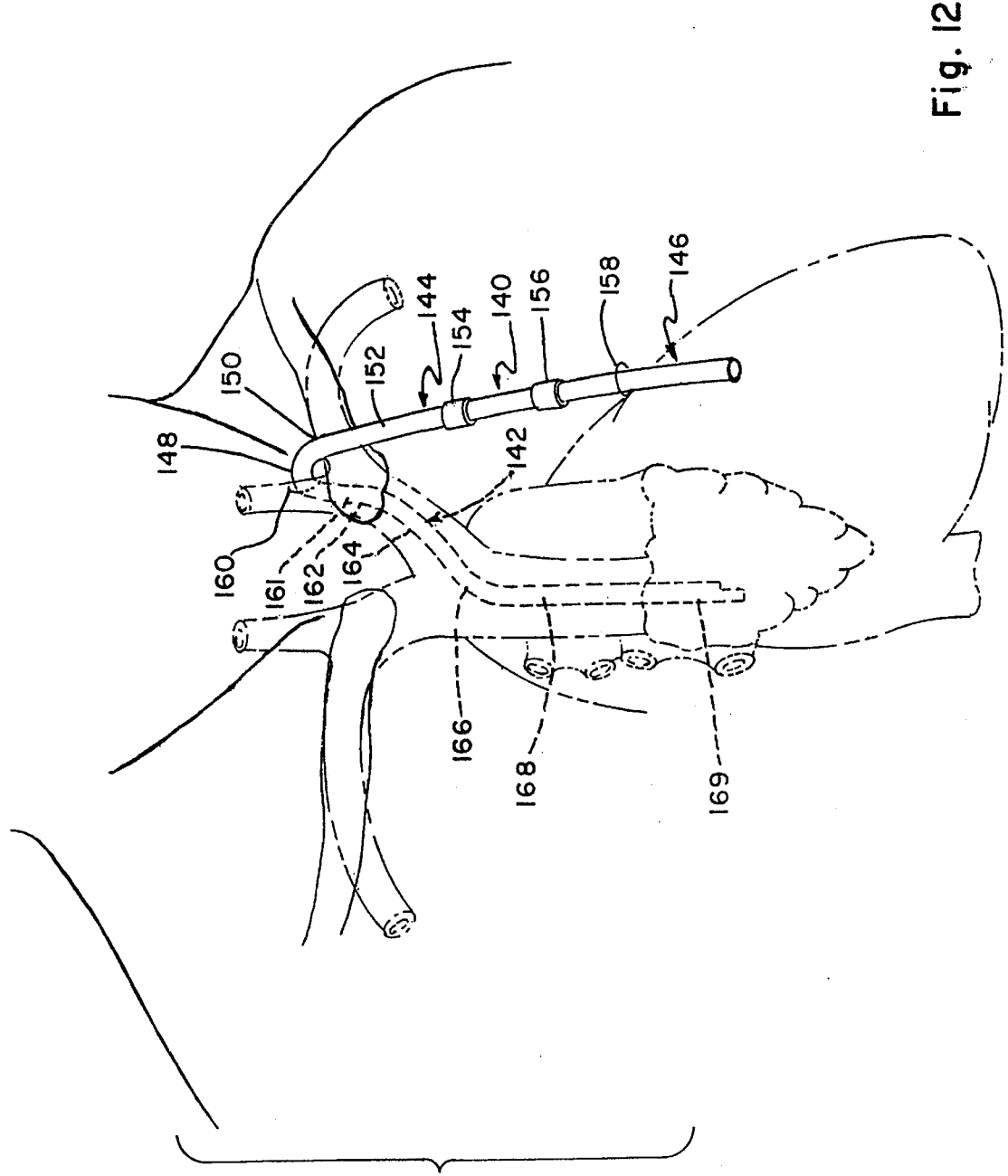
FIG. 12 is an elevational view of the same implanted catheter from an oblique arc angle compared with FIG. 11.

Referring to FIGS. 11 and 12, a catheter 140 for the left jugular vein is disclosed. Catheter 140 defines an intravenous segment 142 with the distal tip thereof 143 shown located in the right atrium 169 of the patient's heart for the advantages discussed above. The proximal end of intravenous segment 142 is found at the entrance 160 of the jugular vein, which is surgically formed, followed by insertion of the catheter. The intramural portion 144 of catheter 140 extends proximally from vein aperture 160 to the skin surface 158, while the external portion 146 extends outwardly from the skin for connection as desired, and particularly with the connector of FIG. 5.

At the junction area between intravenous and intramural segments 142, 144, the catheter defines, in its natural, unstressed condition, a bent, generally U-shaped section 148 which is convex cranially, and which typically defines an arc angle of 160°–180°. Extending from bend 148 distally, a bent portion 161 extends in a clockwise arc in the opposite sense from bend 148, around the tubing axis, extending laterally and anteriorly about 3–30 mm until it traverses left clavicle 150.

Intramural segment 144 extends proximally in section 152 downwardly and approximately 20–80 mm anteriorly, being provided in this embodiment with a pair of cuffs 154, 156, the outer cuff being located in the surgical tunnel about 5–20 mm from skin exit 158.

In the intravenous segment 142, from the entrance 160 to the internal jugular vein, the catheter then completes its arc 148 and extends downwardly about 5–30 mm., then bending medially in arc 161 30–90 degrees in the coronal plane and 5–30 degrees anteriorly in the sagittal plane to enter into left brachiocephalic vein 162. The part of the catheter from entrance 160 into the left brachiocephalic vein extends about 20–100 mm to the vein brachiocephalic apex 163, which is located at the vein crossing the arterial brachiocephalic trunk. At about this apex 163 the catheter segment 164 defines a bend 166 about 20–90 degrees posteriorly and downwardly about 10–70 degrees to extend 10–50 mm to enter into the superior vena cava 169. The catheter then extends downwardly in segment 168 about 20–120 mm in an arc angle of 0–10 degrees posteriorly or anteriorly in the sagittal plane and 0–10 degrees medially or laterally in the coronal plane (ie. substantially straight) so that distal tip 143 occupies the right atrium.

Figure 13:
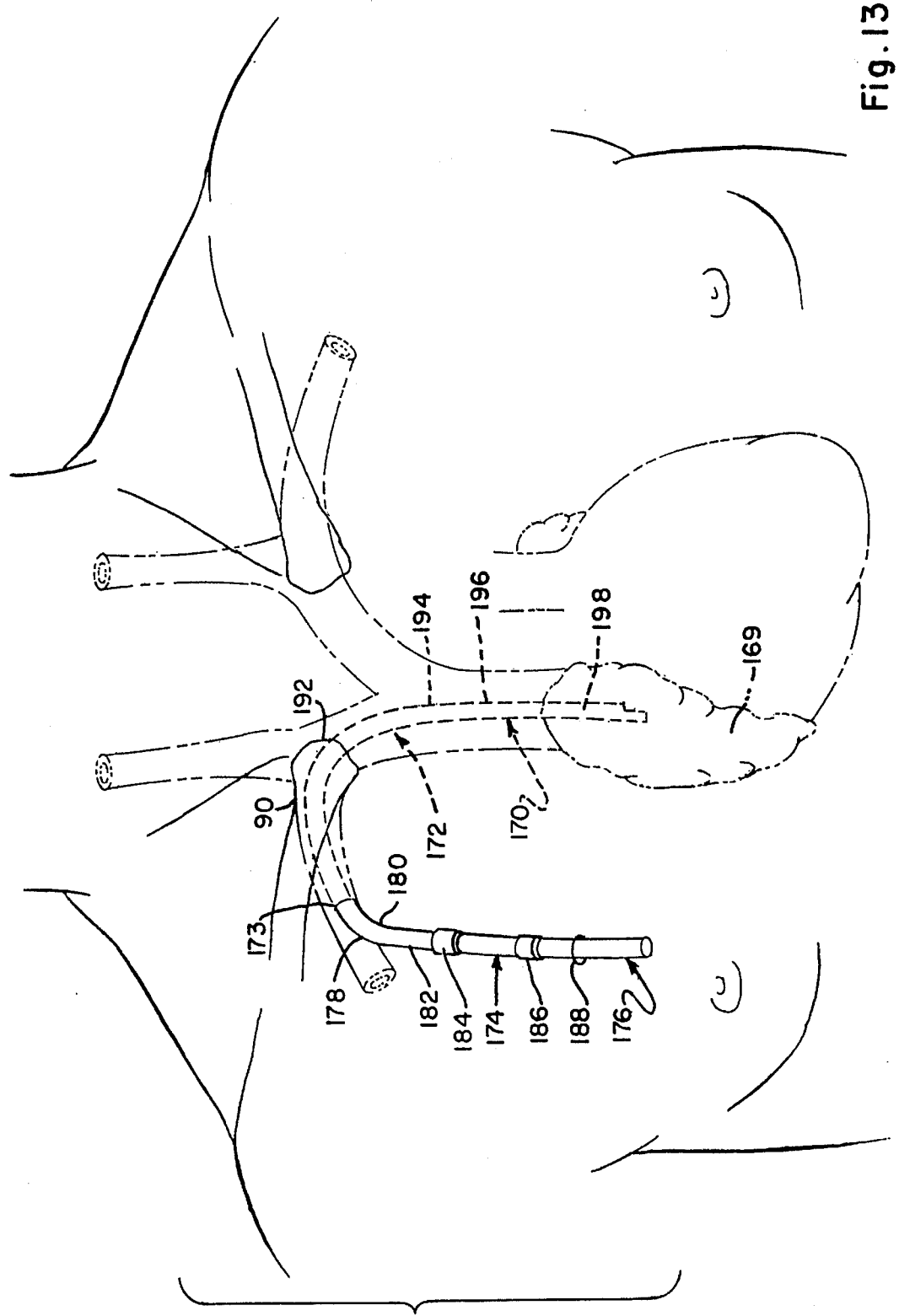
FIG. 13 is an elevational view of another embodiment of the catheter of this invention, shown implanted in the right atrium through the right subclavian vein.
Figure 14:
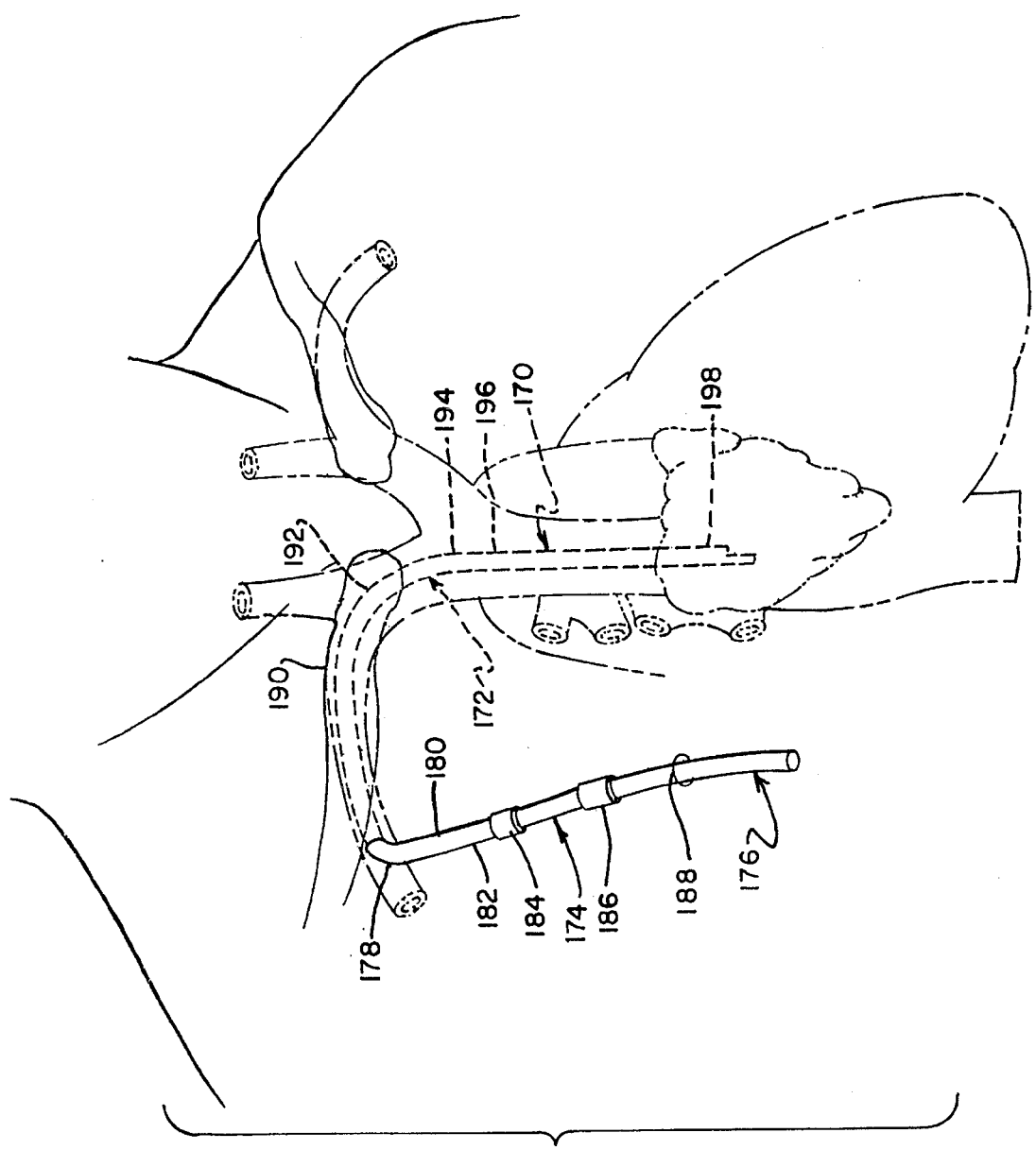
FIG. 14 is an elevational view similar to FIG. 13, taken from an oblique arc angle relative to FIG. 13.

Referring now to FIGS. 13 and 14, a catheter for the right subclavian vein is shown, implanted in its natural, unstressed configuration and extending from such vein to the aorta and into the right atrium 169. Catheter 170 comprises an intravenous segment 172, an intramural segment 174 extending from the access point 173 through the vein wall to the skin outlet 188, and an outwardly projecting, proximal external portion 176 for connection first with a Y portion as shown in FIGS. 5 and 6 and, through that, the dialysis apparatus.

Catheter 172 defines a curved section 178, which is convex upwardly and also bent forwardly (as shown in FIG. 14) defining an arc angle of typically 70–100 degrees, extending downwardly and anteriorly by about 5–30 mm until it reaches subcutaneous tissue in the first intercostal space 180 (FIG. 14). Then, intramural segment 182 extends downwardly about 20–80 mm anteriorly at an arc angle of about 5–30 degrees to the sagitta plane and about 0–20 degrees medially or laterally to the coronal plane. This section of the catheter is provided with a pair of cuffs 184, 186, with cuff 186 being located in the surgically created tunnel about 5–20 mm from skin exit 188.

From entrance 178 into the right subclavian vein 190 the catheter extends in a long arc of about 10–50 mm to the vein apex as indicted at 190, located at the upper border of the right clavicle. At the apex of the right subclavian vein 190, the catheter may bend about 0–10 degrees posteriorly or anteriorly in the sagittal plane and down about 20–80 degrees for about 5–35 mm. to enter into the right brachiocephalic vein 192. Then, the catheter bends about 20–80 degrees in the coronal plane and from 0–10 degrees anteriorly or posteriorly in the sagittal plane for about 5–60 mm to reach the merger point 194 of the brachiocephalic veins. From there, the catheter may extend in a straight line, or it may bend laterally up to 40 degrees and posteriorly or anteriorly in the sagittal plane by up to 10 degrees to enter the superior vena cava 196. From there, the catheter extends in typically a straight line, but with possible deviations of about 10 degrees posteriorly or anteriorly in the sagittal plane or medially or laterally in the coronal plane so that its distal tip 198 enters the right atrium. As before, distal tip 198 may be of a design similar to previous embodiments, for example, a straight tip version as illustrated in FIGS. 7 and 8 without the balloon, in this particular embodiment.

Figure 15:
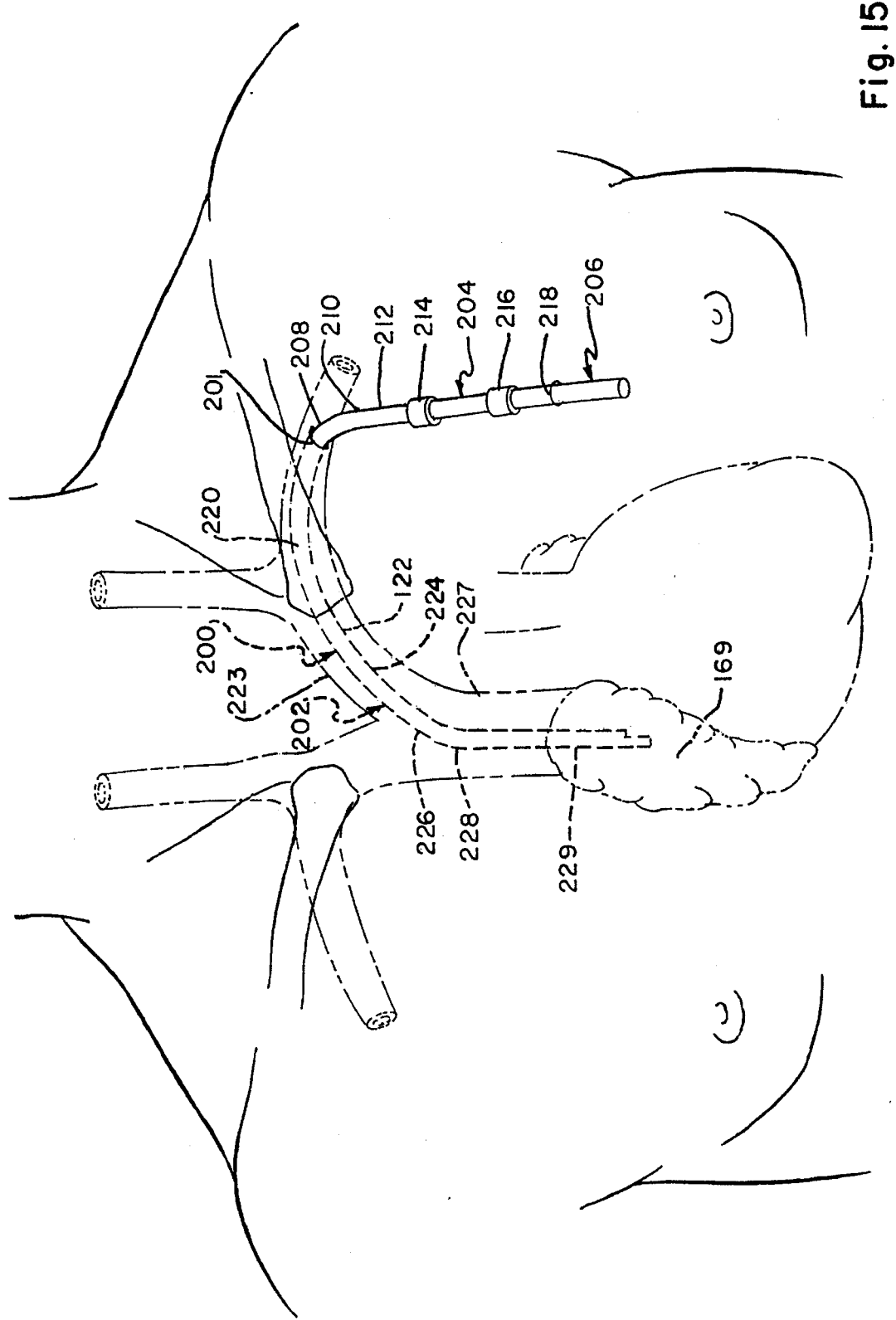
FIG. 15 is an elevational view of another embodiment of the catheter of this invention, shown implanted in the right atrium through the left subclavian vein.
Figure 16:
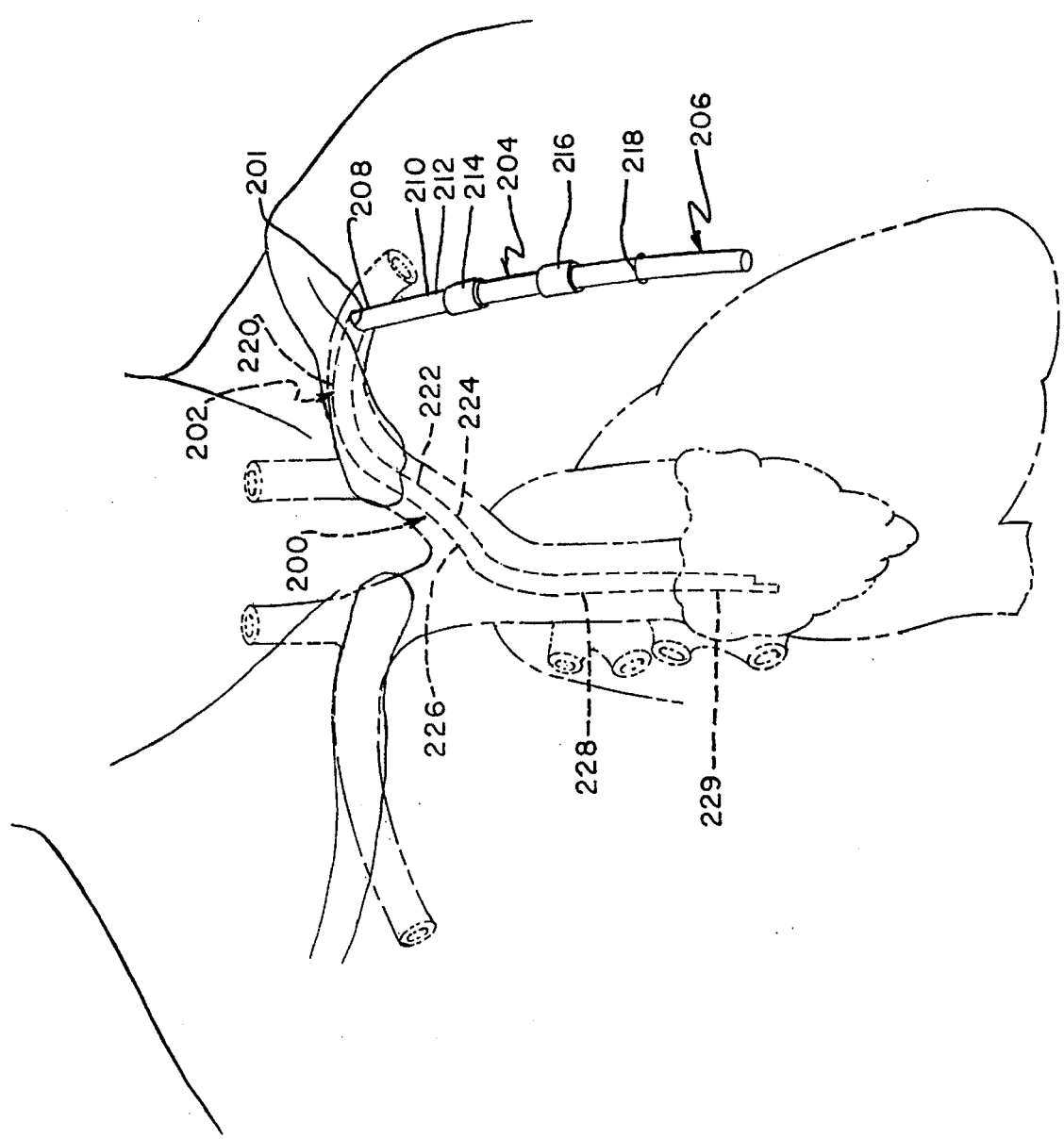
FIG. 16 is an elevational view of the catheter of FIG. 15 taken on an oblique arc angle with respect to FIG. 15.

Referring to FIGS. 15 and 16, a catheter for the left subclavian vein is disclosed, being shown in its natural, unstressed configuration. As before, the distal tip 229 of the catheter reaches into the right atrium 169 from a vein entry site 201 in the left subclavian vein.

Catheter 200 defines, as before, an intravenous segment 202 which terminates proximally at the entry site 201 of the vein; an intramural segment 204 extending through a surgically created tunnel from the vein access site 201 to the skin entry site 218, and an external segment 206 positioned outside of the skin. Catheter 200 is shown in substantially its natural, unstressed condition in which, as in the previous embodiments, its natural shape follows the track of the veins and surgical tunnel in which it is implanted.

In the junction area between intravenous and intramural segments 202, 204, a Curved section 208 is defined which is convex laterally. This section defines an arc angle of 70–130 degrees. Going from the intravenous segment 202 in a proximal direction, the bent section 208 of intramural segment 204 is gradually rotated around the tubing axis about 70–100 degrees clockwise relative to the intravenous segment to extend slightly laterally and downward, and anteriorly about 5–30 mm until it reaches subcutaneous tissue in the first intercostal space 210. Then the intramural segment 204 extends beginning at area 212 downwardly for 20–80 mm anteriorly at an arc angle of 5–30 degrees in the sagittal plane and 0–20 degrees medially or laterally in the coronal plane. This segment is provided with cuffs 214, 216 as in previous embodiments, with outer cuff 216 being located in the tunnel about 5–20 mm from the skin exit 218.

From vein entrance 201 extending distally, the catheter extends upwardly at an arc angle of about 5–15 degrees for about 10–50 mm in area 220 to the vein apex, which is located at the upper border of the left clavicle. Then, the catheter is either straight or bending up to 10 degrees posteriorly or anteriorly in the sagittal plane and down 10–40 degrees for about 5–35 mm to enter into the left brachiocephalic vein, bending down at section 222 about 10–50 degrees in the coronal plane and 5–30 degrees anteriorly in the sagittal plane. The part of the catheter from the entrance into the left brachiocephalic vein 223 extends 20–100 mm. in section 224 to the vein exit, which is located where the vein crosses the arterial brachiocephalic trunk. At the brachiocephalic vein apex the catheter bends in area 224 about 20–90 degrees posteriorly in the sagittal and downwardly 10–70 degrees, extending 10–50 mm. area 226, to enter into the superior vena cava 227. Then, the catheter extends downwardly from point 228 for about 20–120 mm. in a straight line or deviating up to about 10 degrees posteriorly or anteriorly in the sagittal plane or straight, or deviating about 10 degrees medially or laterally in the coronal plane, to enter into the right atrium 169 of the heart.

By forming the catheter in the shape as illustrated and described, great advantage is provided in that irritation of the vein wall by impacting or rubbing of the catheter is minimized.

Figure 17:
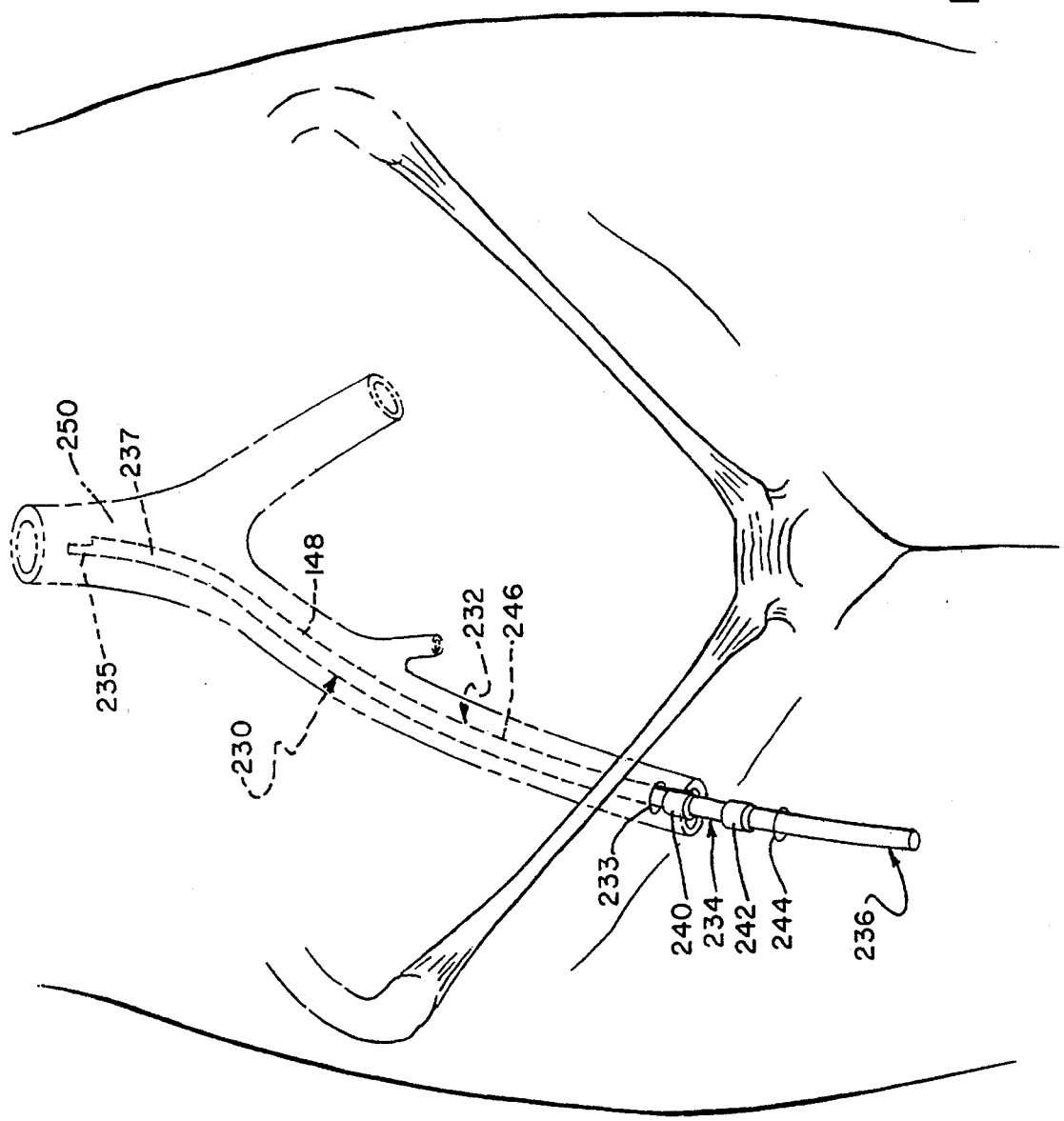
FIG. 17 is another embodiment of the catheter of this invention, shown implanted in the femoral vein of a patient.

Referring to FIG. 17, a catheter 230 for the femoral veins is disclosed. Catheter 230 is shown in its natural, unstressed configuration, implanted into the common iliac vein through the femoral vein. Intravenous segment 232 extends to the access site 233 through the vein wall to catheter distal tip 235, which tip may be similar to the previous embodiments, particularly that of FIGS. 7 and 8 without the balloon.

Intramural catheter portion 234 may be short in this embodiment, extending between catheter access site 233 through a surgically created tunnel to the skin exit 244, where external catheter portion 236 is found. From intravenous segment 232, intramural portion 234 typically extends almost straight down, being provided with a pair of cuffs 240, 242 in the usual manner. The outer cuff 242 is located about 5–20 mm. from the skin exit 244. The intravenous catheter portion 232 defines a curved segment 246 located in the femoral and external iliac veins, extending convex laterally about 10–50 degrees in arc angle, with the catheter extending distally in an upward direction for 50–200 mm. to enter into the common iliac vein, with catheter distal tip 235 being located in the inferior vena cava. Adjacent distal tip 235, a catheter bend 237 is provided in a direction opposite to catheter curved portion 246, the bend comprising and arc of about 20–50 degrees to direct catheter tip 235 upwardly and to extend about 20–50 mm. in the inferior vena cava 250.

FIG. 18 is a cross-sectional view of any of the catheters shown above in FIGS. 1–17, showing a septum 262 dividing the catheter into a pair of semicircular lumens. Inflow lumen 264 collects blood from its distal tip and conveys it to the proximal catheter end which is connected to the dialysis apparatus. Outflow lumen 266 receives dialyzed blood from the dialysis apparatus and conveys it back to the proximal catheter end. For example, in FIG. 1, inflow lumen 264 would be connected to inflow port 26, while outflow lumen 266 would be connected to outflow port 24.

A radiopaque stripe 268 may be provided in the catheter wall adjacent outflow lumen 266 for x-ray visibility.

FIG. 19 discloses an alternative cross-sectional shape that may be provided to the catheters disclosed herein. The oval, extruded catheter cross-section is provided with an inflow lumen 272 and an outflow lumen 274. Radiopaque stripe 276 is also provided, with the catheter of FIG. 19 being used as a substitute design for the catheter of FIG. 18 and otherwise similar in all respects.

Accordingly, a multiple lumen catheter is provided for hemodialysis or any other desired use, which exhibits less clotting and irritation because it causes less damage to the walls of the blood vessel or duct in which it resides, when compared with other prior art catheters. Because of that, less clotting takes place as well, so that the catheter is capable of use as a long-term indwelling catheter for greater periods of time than other catheters of the prior art.

Such catheters may have all the advantages of transcutaneous blood access devices, without significant disadvantages that are found in such devices. The catheters may be used frequently without pain and detriment to the access, yet they will be of reduced susceptibility to clotting and infections.

The above has been offered for illustrative purposes only, and is not intended to limit the scope of the invention of this application, which is as defined in the claims below.

That which is claimed is:

1. The method of implanting a catheter in communication with a blood vessel of a patient, said catheter defining a pair of lumens to permit simultaneous withdrawal and replacement of blood to and from the patient, comprising the step of implanting said catheter in the patient with a proximal portion of the catheter extending through a surgically created tunnel, and a distal portion of said catheter extending through the venous system of said patient So that the distal tip of said catheter occupies the right atrium of the heart of the patient, said catheter, in its unstressed, as-manufactured configuration being of substantial U-shape and defining a central catheter arc and a pair of relatively straight catheter end portions respectively comprising said proximal and distal portions, said catheter penetrating the wall of the vein of said venous system at a position along said U-shaped arc, said catheter substantially occupying said unstressed, as-manufactured configuration in both said venous system and said surgical tunnel, said catheter having a proximal end which extends outwardly from the skin of said patient.

2. The method of claim 1 in which, in said unstressed, as-manufactured configuration, said distal portion of said catheter bends in the dimension perpendicular to said U-shaped central catheter arc.

3. A catheter for hemodialysis which comprises a flexible catheter tube having a distal end and defining a plurality of separate lumens, said catheter defining a first arc angle portion in its natural, unstressed configuration which is substantially coplanar with a major portion of the catheter, said first arc angle portion being spaced from the catheter distal end, said catheter also defining, in its natural, unstressed condition, a second arc angle portion adjacent to said first arc angle portion and positioned between said first arc angle portion and said distal end, said second arc angle portion extending in a direction substantially perpendicular to the direction of said first arc angle portion, said catheter being adapted to be positioned in the femoral vein, said catheter being of a length to permit positioning of the distal catheter end in the inferior vena cava when the catheter is placed in the femoral vein, said first arc angle portion being of essentially 10° to 50° and extending essentially 50–200 mm, said second arc angle portion defining an arc of essentially 20° to 50° and extending essentially 20–50 mm, said catheter defining a shape, in its natural, unstressed condition, which is substantially of the shape of said femoral vein and inferior vena cava, whereby portions of said catheter do not press against vein walls.

4. The method of implanting an indwelling, multiple lumen, venous catheter which comprises: making an incision from the skin to a desired access site; inserting a distal portion of the catheter through the access site and further on into the patient; making a surgical tunnel outwardly through tissue from said access site, said tunnel having an inner end at the vicinity of the access site and having an outer end extending through the skin; inserting a proximal portion of said catheter into said tunnel from the inner end, and advancing it outwardly whereby said proximal portion passes outwardly from the tunnel through the skin; and attaching to the catheter proximal end a multiple tube connector extension member having tubes that separately connect with separate catheter lumens.

5. The method of claim 4 in which said access site is a vein wall, and the catheter carries at least one tissue penetrable securance cuff, positioned on said catheter so that said cuff resides in the surgical tunnel but never passes through the skin at the outer end of said surgical tunnel.

6. The method of claim 4 in which said catheter, in its natural, unstressed configuration, defines an arc angle of generally U-shape positioned between a pair of relatively straight terminal catheter sections.

7. The catheter of claim 6 in which one portion of said relatively straight terminal catheter sections bends in the dimension perpendicular to said U-shaped arc angle of the catheter.

* * * * *